United States Patent
Chen et al.

(10) Patent No.: US 12,124,452 B1
(45) Date of Patent: Oct. 22, 2024

(54) MATERIALS INFORMATION DATABASE INCLUDING MACHINE LEARNING MODELS

(71) Applicant: Microsoft Technology Licensing, LLC, Redmond, WA (US)

(72) Inventors: Chi Chen, Renton, WA (US); Hongbin Liu, Redmond, WA (US); Andrea Cepellotti, Arlington, MA (US); Mark A Woodlief, Duvall, WA (US); Nihit Pokhrel, Seattle, WA (US); Adrian Dumitrascu, Redmond, WA (US); Matthias Troyer, Clyde Hill, WA (US); Nathan Andrew Baker, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/321,415

(22) Filed: May 22, 2023

(51) Int. Cl.
*G06F 16/24* (2019.01)
*G06F 16/2453* (2019.01)
*G06F 16/2455* (2019.01)
*G06F 16/248* (2019.01)

(52) U.S. Cl.
CPC .... *G06F 16/2455* (2019.01); *G06F 16/24542* (2019.01); *G06F 16/248* (2019.01)

(58) Field of Classification Search
CPC ........... G06F 16/2455; G06F 16/24542; G06F 16/248
See application file for complete search history.

(56) References Cited

U.S. PATENT DOCUMENTS

| | | | |
|---|---|---|---|
| 11,282,291 B1* | 3/2022 | Boardman | G06T 1/0007 |
| 2020/0257933 A1* | 8/2020 | Steingrimsson | C22C 30/00 |
| 2022/0254045 A1* | 8/2022 | Boardman | G06T 17/00 |
| 2022/0301192 A1* | 9/2022 | Boardman | G06T 7/579 |
| 2023/0191608 A1* | 6/2023 | Horowitz | B25J 9/163 |
| | | | 700/245 |
| 2023/0192416 A1* | 6/2023 | Horowitz | B25J 9/1697 |
| | | | 700/223 |

(Continued)

OTHER PUBLICATIONS

Chen, et al., "A Universal Graph Deep Learning Interatomic Potential for the Periodic Table", In Repository of arXiv:2202.02450v2, Aug. 14, 2022, 58 Pages.

(Continued)

*Primary Examiner* — Eliyah S. Harper
(74) *Attorney, Agent, or Firm* — Alleman Hall & Tuttle LLP (57) ABSTRACT

Examples are disclosed that relate to materials discovery using machine learning models. One example provides a method enacted on a computing system. The method comprises receiving a query comprising one or more of element information and material property information, and, based on the query, retrieving material data from a materials information database. The material data comprises structural information for each material within a set of materials matching the query, the set comprising one or more materials, and for one or more materials in the set of materials, one or more predicted material properties determined using one or more trained machine learning models. The method further comprises outputting the material data.

20 Claims, 8 Drawing Sheets

(56) References Cited

U.S. PATENT DOCUMENTS

2023/0214583 A1* 7/2023 Sawyer ............ G06V 30/19173
2024/0073831 A1* 2/2024 Fahim ................ H04W 52/362

OTHER PUBLICATIONS

Andersen, et al., "Optimade, an API for exchanging materials data," Scientific Data, vol. 8, Issue No. 1, Aug. 12, 2021, pp. 1-10.
Chibani, et al., "Machine learning approaches for the prediction of materials properties," Apl Materials, vol. 8, Issue No. 8, Aug. 1, 2020, pp. 1-10.
International Search Report and Written Opinion received for PCT Application No. PCT/US2024/026121, Aug. 12, 2024, 11 pages.
Ward, et al., "Matminer: An open-source toolkit for materials data mining," Computational Materials Science, vol. 152, May 25, 2018, pp. 60-69.

* cited by examiner

| ID | Formula | Structure | | Bandgap (eV) | | |
|---|---|---|---|---|---|---|
| | | Type | Sites | Value | Method | Uncertainty |
| mat1 | $Fe_2O_3$ | Crystal | 10 | 2.2 | Exp. | 0.0 |
| mat2 | C | Crystal | 2 | 4.1 | DFT/PBE | 0.0 |
| mat3 | $Al_2O_3$ | Crystal | 10 | 5.7 | ML | 0.1 |
| mat4 | NiO | Crystal | 2 | 3.8 | Exp. | 0.0 |
| mat5 | $H_2O$ | Molecule | 3 | - | DFT/ZORA-BLYP-D3(BJ)/TZ2P | - |

FIG. 3

| ID | Formula | Structure | | Bandgap (eV) | | |
|---|---|---|---|---|---|---|
| | | Type | Sites | Value | Method | Uncertainty |
| Gen-1 | $A_2M_xM_yO_4$ | Crystal | 8 | 2.1 | ML | 0.3 |
| Gen-2 | $A_3M_{x2}M_yO_5$ | Crystal | 22 | 3.1 | ML | 0.6 |
| Gen-3 | $A_3M_xM_{y2}O_6$ | Crystal | 36 | 2.3 | ML | 0.4 |
| Gen-4 | $AM_{x3}M_{y2}O_8$ | Crystal | 28 | 2.2 | ML | 0.3 |

MATERIALS INFORMATION DATABASE INCLUDING MACHINE LEARNING MODELS

BACKGROUND

Information databases can be used to help search for materials having a desired property or desired elemental composition. However, data exists for a small subset of accessible material space. Further, experimental material data of some materials may be incomplete. For example, some material properties may be missing.

SUMMARY

Examples are disclosed that relate to materials discovery using machine learning models. One example provides a method enacted on a computing system. The method comprises receiving a query comprising one or more of element information and material property information, and, based on the query, retrieving material data from a materials information database. The material data comprises structural information for each material within a set of materials matching the query, the set comprising one or more materials, and for one or more materials in the set of materials, one or more predicted material properties determined using one or more trained machine learning models. The method further comprises outputting the material data.

Another example provides a method enacted on a computing system, the method comprising receiving a query comprising element information, and inputting the element information into a trained generative machine learning model to generate a plurality of candidate structures based on the element information. The method further comprises, for one or more candidate structures of the plurality of candidate structures, inputting the candidate structure into a second trained machine learning model configured to perform structural relaxation and output a relaxed candidate structure, inputting the relaxed candidate structure into a third trained machine learning model configured to output a predicted material property, and outputting the relaxed candidate structure and the predicted material property.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Materials discovery can be seen as a search problem in the vast chemical space. However, materials discovery can be difficult due to slow trial-and-error research approaches and high cost of material synthesis and experimentation. Previously, quantum mechanics (QM) calculations have been successful in finding new molecules or materials that satisfy property requirements. However, QM calculations can have high computational cost which can limit search space. A further complication to materials discovery is the size of unexplored chemical space. For example, regarding molecules, estimates for accessible chemical space of small organic molecules≤30 atoms range from $10^{20}$ to $10^{24}$, whereas the largest databases comprise information for fewer than $10^{12}$ molecules. Likewise, regarding solid state materials, data exists for a small subset of accessible material space. As a particular example, the Materials Project database comprises information for fewer than 200,000 materials (Anubhav Jain, Shyue Ping Ong. Geoffroy Hautier. Wei Chen, William Davidson Richards, Stephen Dacek, Shreyas Cholia, Dan Gunter, David Skinner, Gerbrand Ceder, Kristin A. Persson; Commentary: The Materials Project: A materials genome approach to accelerating materials innovation. *APL Mater* 1 Jul. 2013; 1 (1): 011002). Further, experimental material data of some materials may be incomplete, i.e., some material properties may be missing.

In recent years, artificial intelligence (AI), in particular machine learning, is starting to be used for learning the quantitative structure-property relationship (QSPR) in small molecules and solid-state crystalline materials. Machine learning techniques can be orders of magnitude faster than QM calculations. However, machine learning models can suffer from lack of training data. The effectiveness of machine learning for materials discovery depends on the quality and quantity of training data. QM calculations can be used to generate such training data. However, a brute force approach that uses QM calculations to explore material space may be impractical. Further, such approaches may not target useful areas of material space.

Accordingly, examples are disclosed that relate to an interactive materials discovery platform comprising machine learning models and a materials information database. The materials discovery platform can incorporate machine learning inference, database searching, quantum mechanics calculations, and machine learning training in a loop for accelerating the discovery of new materials. The discovery workflow uses data generated by user-directed discoveries to grow the materials information database and improve the machine learning models. As described in more detail below, the materials information database comprises material data for a plurality of materials. For each material, the material data comprises structural information and material property information. For at least some materials in the materials information database, the material data comprises predicted values for one or more material properties. Material properties are predicted using corresponding trained machine learning models. A user can query a materials information database to discover materials with a selected elemental composition and/or selected material property.

The interactive materials discovery platform also can include generative machine learning models to generate candidate structures for materials that are not listed in the materials information database. As an example, a user query may retrieve a small number of matches, or no matches. In response, a generative machine learning model can be used to generate candidate structures based on the elemental information of the user query. A property prediction pipeline is then used to predict one or more material properties for the candidate structures. The property prediction pipeline can comprise machine learning models for structural relaxation of candidate structures, machine learning models for material property predictions, uncertainty estimation, and/or quantum mechanics calculations. Data for the candidate structures can then be inserted into the materials information database. Quantum mechanics-calculated values can be used to further train the machine learning models. In this manner, the interactive machine learning models can be further improved with continued use of the materials discovery platform. By performing QM calculations in response to user-directed queries, the machine learning models can be further trained using data from more relevant areas of unexplored material space.

Figure 1:
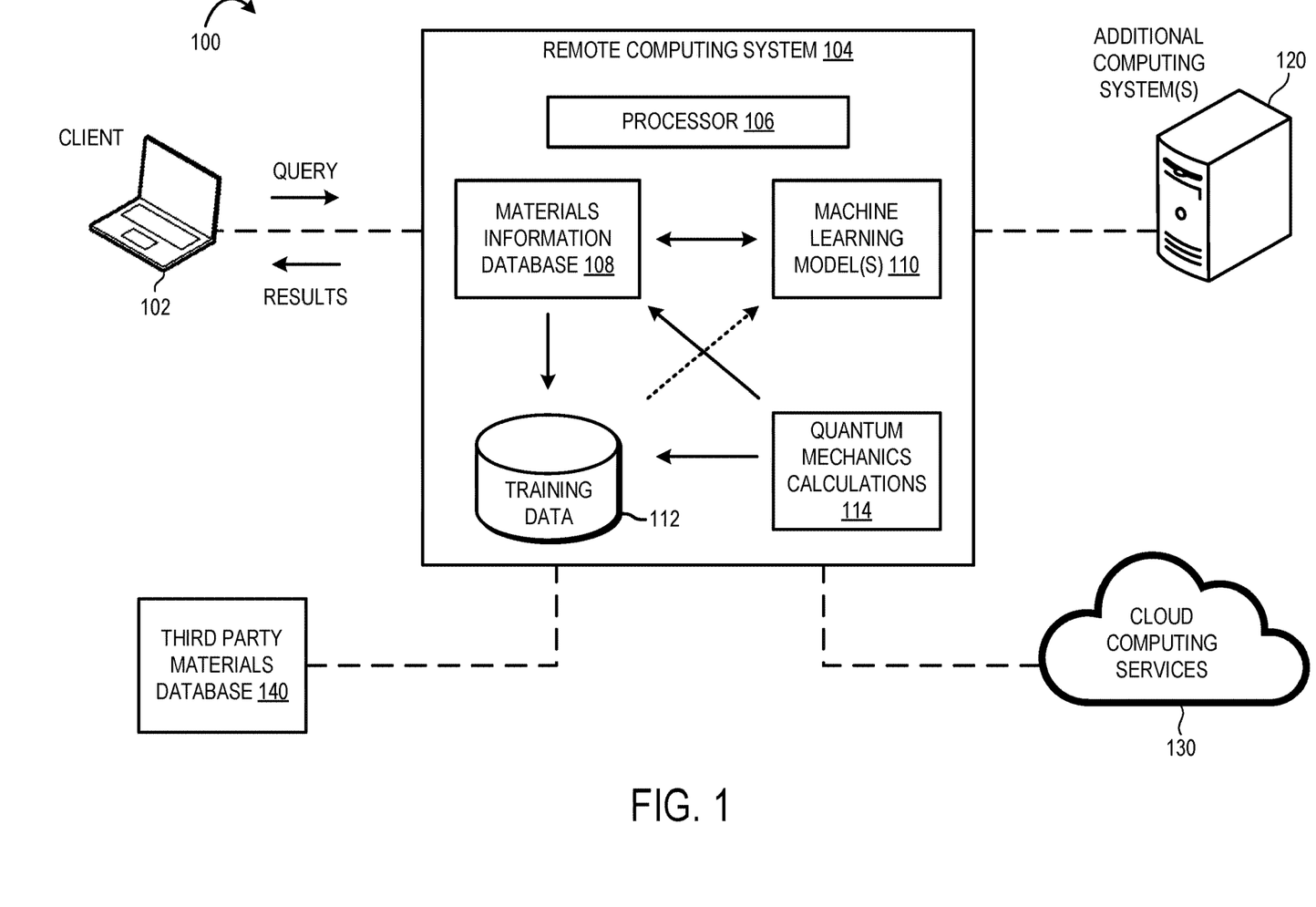
FIG. 1 schematically shows an example computing architecture for implementing an interactive materials discovery platform.

Prior to discussing these examples in detail, FIG. 1 shows an example computing architecture 100 for implementing an interactive materials discovery platform. As illustrated in FIG. 1, a client computer 102 can submit a query to a remote computing system 104. Remote computing system 104 comprises one or more processors 106 configured to process queries and perform various other functions. A method of processing queries is discussed below with regard to FIG. 2. Remote computing system 104 can represent a data center in some examples. Examples of computing systems are described in more detail below with regard to FIG. 7.

Remote computing system 104 further comprises a storage subsystem storing data for a materials information database 108, one or more machine learning models 110, and training data 112. Materials information database 108 comprises data for a plurality of materials, including predicted material properties determined using machine learning models 110. Details of the materials information database are discussed below with regard to FIG. 3.

Machine learning models 110 comprises a plurality of machine learning models for predicting material properties. For a selected material property, one or more machine learning models can be trained using training data 112 to predict the selected material property. In this manner, machine learning models 110 are used to augment the material data in materials information database 108.

A trained machine learning model can be configured to output a material property prediction based on an input of a material structure. Material structures can be represented in any suitable manner, such as a graph. In an example graph, nodes represent atoms and edges represent chemical bonds. Example output of a machine learning model can comprise material properties data (e.g., bandgap, dielectric constant) and constituent atom or ion data (e.g., properties of atoms/ions in the material structure, such as ionic radii, atomic number, atomic mass, electron configuration, charge, etc.). Any suitable machine learning architecture can be used. Examples of suitable architectures for a machine learning model include neural networks (NN) and random forests. One particular example of a NN is a graph neural network (GNN). GNNs are trained to perform inference on data described by a mathematical graph. Graphs can be a suitable choice for representing a crystal (e.g. a unit cell of a crystal), where nodes represent atoms and edges represent bonds. In some examples, a representation of a material structure can comprise one or more of a space group, a lattice structure, atomic positions, interatomic distances, bond angles, and symmetry information. In some examples, material information is encoded using an encoding scheme. For example, an interatomic distance can be encoded and represented by an edge of a graph. Further an atom type can be represented by a chemical symbol or atomic number, as examples. In some examples, an encoding can be used to represent two or more atoms as a single unit, such as a polyatomic ion or functional group.

Machine learning models 110 can be trained on training data 112 using any suitable method. In some examples, a machine learning model can be trained using supervised learning. Supervised learning comprises training a machine learning model using corresponding input (e.g., a material structure) and output values (e.g., a material property value). In various examples, supervised learning can comprise regression-type prediction problems and classification-type prediction problems. Regression techniques comprise predictions of a variable that is continuous, such as a bandgap, a bulk modulus, or a dielectric constant. Classification tasks comprise predictions of a categorical variable, such as metal vs. non-metal or conducting vs. insulating. Machine learning models can comprise any suitable algorithms. Examples of regression learning algorithms include linear regression, regression trees, and support vector machines. Examples of classification algorithms include k-nearest neighbor, naïve Bayes, and decision trees. In some examples, the machine learning model is a feedforward neural network. Feedforward NNs can be trained using back propagation to compute the gradient of a loss function.

Machine learning models 110 each can be configured for predicting a material property. Examples include a predicted band gap, a predicted conductivity, a predicted bulk modulus, a predicted shear modulus, a predicted formation energy, a predicted phonon density of states peak, a predicted dielectric constant, and a predicted refractive index. As a specific example, a machine learning model for predictions of bandgaps for perovskite structures using crystal site feature embedding is described in Hitarth Choubisa, Mikhail Askerka, Kevin Ryczko, Oleksandr Voznyy, Kyle Mills, Isaac Tamblyn, Edward H. Sargent, Crystal Site Feature Embedding Enables Exploration of Large Chemical Spaces, *Matter*, Volume 3, Issue 2, 2020, Pages 433-448. In some examples, each predicted material property is predicted using a corresponding trained machine learning model. In some examples, a selected material property is predicted using a plurality of trained machine learning models, or an ensemble of machine learning models. In some such examples, each trained machine learning model of the ensemble of trained machine learning models comprises different hyperparameters. In some examples, each trained machine learning model of the ensemble of trained machine learning models is trained on the same training data. In some other examples, each trained machine learning model of the ensemble of trained machine learning models is trained on different training data, e.g., a different subset of training data.

In some examples, machine learning models 110 can be used to determine an uncertainty for a predicted material property. Any suitable method can be used for estimating uncertainty. In some examples, an ensemble of trained machine learning models is used to determine an ensemble of values for a predicted material property, and the uncertainty is estimated based on the ensemble of values.

Training data 112 used to train machine learning models 110 comprises material information for a plurality of materials. For each material in training data 112, the material information comprises structural information and material property information. The material property information can comprise experimentally determined values and/or QM-calculated values. As described below, additional material data can be added to training data 112 based on QM calculations 114.

Continuing, remote computing system 104 further can hold instructions for performing QM calculations 114. QM calculations 114 can utilize any suitable method. Examples include Hartree-Fock methods (HF), Moller-Plesset perturbation theory (MP2), and DFT methods. DFT methods may utilize any suitable approximation to the exchange and correlation functionals, such as the local density approximation (LDA), generalized gradient approximation (GGA), hybrid functionals (e.g., B3LYP, PBE0), meta-GGA functionals, or meta-hybrid functionals (e.g., M06-L). QM calculations can be performed using any suitable basis sets, such as Gaussian type orbitals and/or planewaves. Further, QM calculations can be performed using any suitable convergence criteria. In some examples, a QM calculation comprises performing a basis set convergence. In some examples, a QM calculation comprises performing a k-point convergence. In some examples, the method used for a QM calculation is dependent on the structure of the material. For example, a QM calculation of graphite can include a correction to account for Van der Waals forces whereas such a correction can be omitted for a calculation of diamond. In some examples, the method used for a QM calculation is dependent on the material property being calculated. For example, a QM calculation of magnetic properties can comprise performing a spin polarized calculation. Then, upon determining a material is non-magnetic, a QM calculation of bulk modulus can comprise performing a non-spin polarized calculation.

In some examples, results from QM calculations 114 are added to materials information database 108. Further, in some examples, results from QM calculations 114 are added to training data 112 and used to further train machine learning models 110. This process is discussed in more detail below with regard to FIG. 2.

Continuing, remote computing system 104 can communicate with one or more additional computing system(s) 120, cloud computing services 130, and one or more third-party materials databases 140. In some examples, remote computing system 104 can offload processing tasks to additional computing system(s) 120 and cloud computing services 130. For example, additional computing system(s) 120 and cloud computing services 130 can be configured for using machine learning models to determine a predicted material property, training machine learning models, or performing QM calculations. Further, remote computing system 104 also can retrieve material data for one or more materials from third-party materials database 140. In some such examples, material information retrieved from third-party materials database 140 can be used to update materials information database 108 or training data 112. For example, experimental data retrieved from a third-party materials database 140 can be added to training data 112 and used to further train machine learning models 110.

Figure 2:
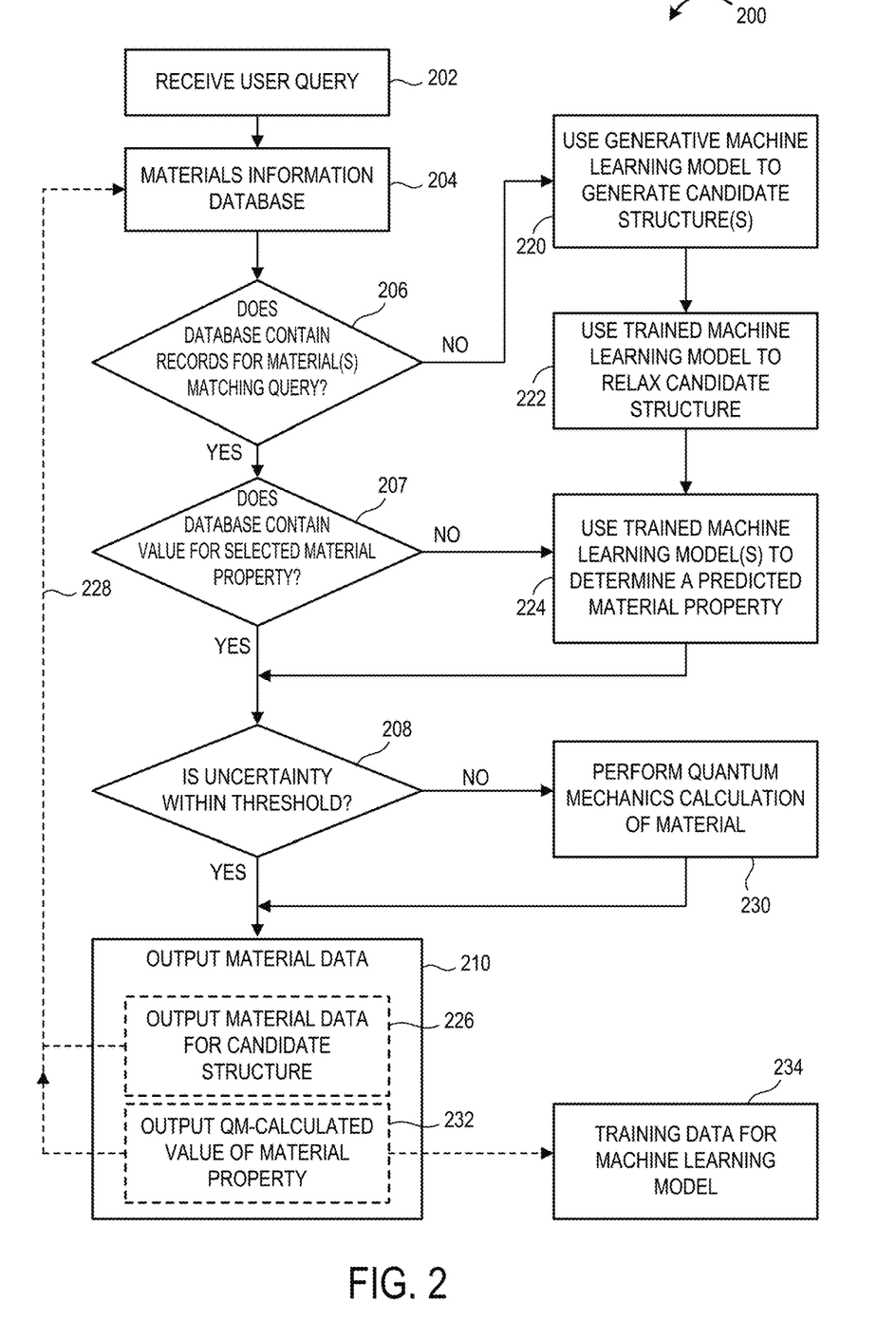
FIG. 2 shows a flow diagram for an example method of processing a query.

As mentioned above, a user can query a materials information database to discover materials. FIG. 2 shows a flow diagram of an example method 200 for processing queries on an interactive materials discovery platform that includes a cycle for adding new material properties to the database using QM calculation. Method 200 can be enacted on one or more computing systems using distributed computing or cloud computing, as examples. Method 200 is an example of a method that can be implemented on remote computing system 104, for example, in response to a query from client computer 102.

Method 200 comprises receiving a user query at 202. The user query comprises one or more of element information and material property information. In some examples, natural language processing (NLP) can be used to process a query. For example, the user query can be input into a large language model configured to process the user query and extract the element information and/or material property information. Element information relates to the elemental composition of a material. In some examples, the element information comprises a list of elements present at any suitable concentration level in a material. In some examples, the element information specifies a concentration range of elements in a material. In some more specific examples, the element information comprises a chemical formula. Material property information relates to one or more material properties. In some examples, material property information can comprise a value or range of values of a material property for a desired material.

Figure 3:
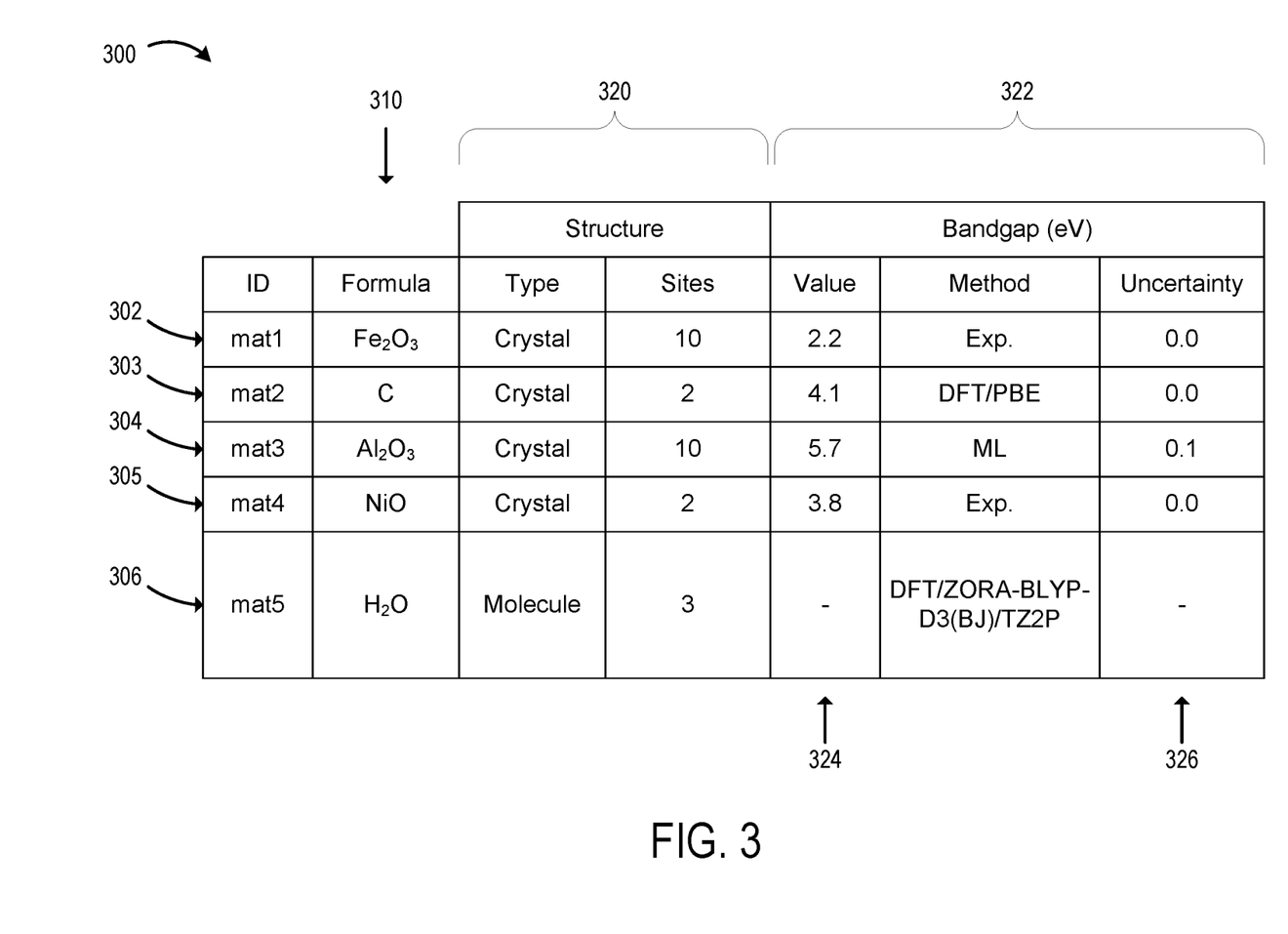
FIG. 3 shows a table representing example material data from a materials information database that includes material properties predicted using machine learning models.

Examples of user queries are discussed in regard to FIG. 3. FIG. 3 shows example material data 300 for a set of materials in a materials information database (e.g., materials information database 108). In the depicted example, material data 300 comprises records for materials 302, 303, 304, 305, and 306. Material data 300 further comprises formulas 310, structural information 320 and property information 322 for each of materials 302, 303, 304, 305, 306. Structural information 320 comprises information related to the material structure of each material in the materials information database. For example, material 302 comprises iron (III) oxide ($Fe_2O_3$). The structural information 320 for $Fe_2O_3$ indicates that the structure is a crystal with 10 lattice sites in the unit cell. Structural information 320 also can comprise information not shown in FIG. 3. For example, additional structural information can include a molecular symmetry group, bond lengths, bond angles, a material space group, unit cell lattice constants, unit cell lattice vectors, coordinates for each site within the unit cell, element information for each atom occupying a site in the unit cell, and other information. In general, each material listed in the materials information database comprises a distinct structure. However, in some examples, different materials can comprise relatively small variations in structure.

Property information 322 comprises information related to one or more material properties. Examples of property information include numerical values, spectral data, and categorical data (e.g., metal or non-metal). As shown in FIG. 3, property information 322 comprises bandgap values 324 for each of materials 302, 303, 304, 305, 306. Property information 322 also comprises information related to the determination of the property value. For example, the bandgap of material 302 ($Fe_2O_3$) is 2.2 eV as determined experimentally. Further, the bandgap of material 303 (C) is 4.1 eV as determined by DFT/PBE (DFT using Perdew-Burke-Ernzerhof (PBE) exchange-correlation functionals). The materials information database also can comprise information for molecules. For example, material 306 comprises $H_2O$. As material 306 is a molecule, the bandgap is not applicable. However, in examples comprising molecular crystals, the materials information can comprise bandgap information.

For at least some materials in the materials information database, the material data comprises a predicted property value determined by a machine learning model. In the example shown in FIG. 3, material 304 ($Al_2O_3$) comprises a bandgap of 5.7 eV as predicted using a trained machine learning model. For ML-predicted properties, the material data 300 comprises an uncertainty 326. In the depicted example, the uncertainty of the ML-predicted bandgap for material 304 is 0.1 eV.

Returning to FIG. 2, based on the user query, method 200 comprises retrieving material data from a materials information database at 204. At 206, method 200 comprises determining if the materials information database contains records for one or more materials matching the query. If records matching the query exist in the materials information database, method 200 can comprise retrieving the corresponding material data from the materials information database.

In some examples, the materials information database comprises partial material data for a selected material matching the user query. However, the material data for the selected material may lack material property information associated with the user query. Thus, at 207, method 200 optionally comprises determining if the material data for a selected material contains a value for the material property associated with the user query. If the material data comprises the desired material property information, method 200 can proceed to 208. However, if the material data lacks information regarding the desired material property, a machine learning model can be used to generate the missing data, as described below at 224.

As an illustrative example, a user query can comprise element information indicating materials comprising iron (Fe) and oxygen (O). Referring again to FIG. 3, material data 300 comprises information for a material matching the elemental information. Thus, in response to the query, material data for material 302 ($Fe_2O_3$) can be retrieved. As a second illustrative example, a user query can comprise material property information indicating a bandgap within a range of 5.5 to 6.0 eV. As material data 300 comprises information for a material matching the specified band gap, material data for material 304 ($Al_2O_3$) can be retrieved.

Returning to FIG. 2, if it is determined that the materials information database comprises information for materials matching the query, at 208, method 200 optionally comprises determining if an uncertainty for a predicted material property is within a threshold uncertainty. In some examples, the threshold uncertainty is a user-selected threshold. In some such examples, the user query can comprise an indication of a threshold, e.g., a threshold value or threshold percentage. If the uncertainty for the predicted material property is within the threshold, method 200 comprises outputting the material data at 210. In some examples, such as when no uncertainty threshold is provided, step 208 can be omitted.

Returning to step 206, if it is determined that the materials information database does not contain records for a material matching the user query, method 200 comprises, at 220, using one or more trained generative machine learning models to generate one or more candidate structures. In some examples, method 200 can proceed to step 220 if the number of records for materials matching the query is below a threshold. In further examples, method 200 can comprise using a trained generative machine learning model to generate one or more candidate structures based on a user request. The trained generative machine learning model is configured to generate candidate structures based on the element information. In some examples, the trained generative machine learning model uses skeleton structures to generate candidate structures. A skeleton structure comprises structural information for one or more different crystal lattices each comprising lattice sites for atoms. In some examples, the skeleton structure comprises charges associated with lattice sites of the skeleton structure. As one example, a perovskite skeleton structure can be used to generate a candidate structure for a material having a formula $AMO_3$, where A and M are different metals. In other examples, any other suitable method for generating candidate structures can be used.

Figure 4:
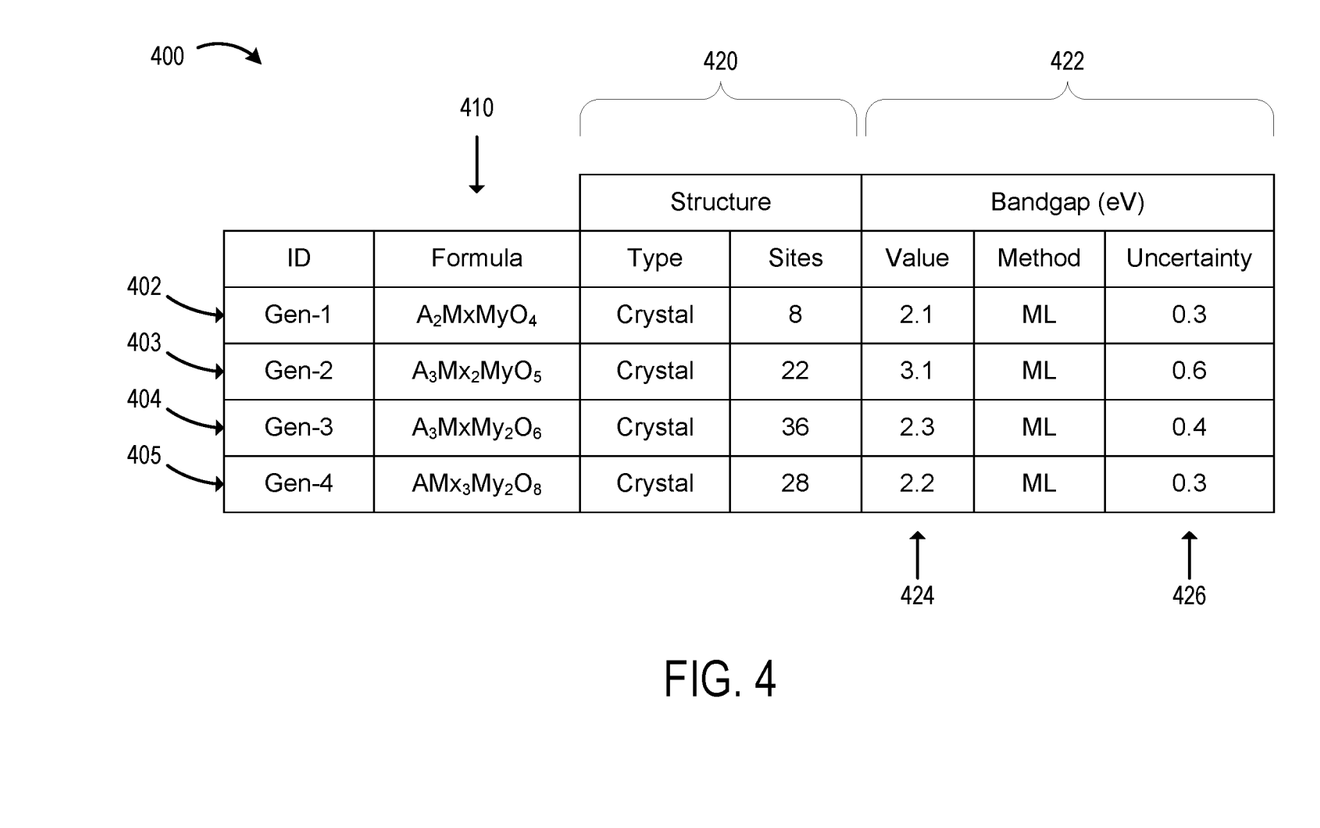
FIG. 4 shows a table representing example material data for materials generated using machine learning models.

FIG. 4 shows example material data 400 for candidate structures generated in response to a user query including element information comprising a combination of elements A, Mx, My, and oxygen (O), where A represents an alkaline metal and Mx and My represent different transition metals. In this illustrative example, no records are found in the materials information database for materials matching the element information. Thus, a trained generative machine learning model is used to generate candidate structures based on the element information. As a result, the trained generative machine learning model outputs a candidate structure for each of generated materials 402, 403, 404, 405. The material data 400 also includes formulas 410 and structural information 420 corresponding to the candidate structures for generated materials 402, 403, 404, 405.

Returning to FIG. 2, after generating one or more candidate structures, method 200 comprises, at 222, using a trained machine learning model to relax the one or more candidate structures. The trained machine learning model used at 222 can comprise any suitable machine learning model, such as those described above. In some examples, the trained machine learning model comprises a GNN with ML-trained interatomic potentials. One example of a trained machine learning model configured to perform structural relaxation is described in Chen. C., Ong, S. P. "A universal graph deep learning interatomic potential for the periodic table," *Nature Computational Science* 2. 718-728 (2022). In other examples, any other suitable method can be used to perform structural relaxation on candidate structures. Examples include energy minimization methods using interatomic potentials, and QM calculations.

After structural relaxation, method 200 comprises using one or more trained machine learning models to determine one or more predicted material properties for a relaxed candidate structure. In some examples, the predicted material property corresponds to the material property information of the user query. For example, if a user query indicates a bandgap as a selected material property, a trained machine learning model configured to predict a bandgap can be used to determine a predicted bandgap for the relaxed candidate structure. In some examples, method 200 further comprises determining an uncertainty for the predicted material property. Examples of determining uncertainty for a predicted material property are described above.

Referring again to FIG. 4, material data 400 also shows predicted material properties for the generated materials 402, 403, 404, 405. To obtain predicted material properties, structural information (e.g., a graph) for candidate structures corresponding to generated materials 402, 403, 404, 405 are input into a trained machine learning model configured to perform structural relaxation. Then, each relaxed candidate structure is input into a trained machine learning model configured to output predicted bandgaps. Example bandgap values are shown as material property information 422 comprising bandgap values 424 and corresponding uncertainties 426 for each generated material 402, 403, 404, 405. Bandgap values 424 are for illustrative purposes and do not indicate actual results from a trained machine learning model.

As mentioned above, the materials information database can comprise partial data for materials in some examples. If the materials information database comprises structural information for a material matching the user query, but information regarding a selected material property is missing for the material, method 200 can proceed from 207 to 224. In such examples, structural information for the selected material can be input into a corresponding trained machine learning model configured to output a predicted value for the selected material property.

After determining the predicted material property for the candidate structure, method 200 comprises, at 208, determining if the uncertainty for the predicted material property is within a threshold. If "YES", method 200 comprises outputting the material data for the candidate structure at 226. In some examples, the material data for the candidate structure is inserted into the materials information database, as indicated by the arrow 228. For example, material data 400 can be added to the materials information database. In this manner, material data for new materials generated in response to a user query can be added to the materials information database.

Returning to 210, if it is determined that the uncertainty for a predicted material property is not within the threshold, method 200 optionally comprises, at 230, performing a QM calculation to determine a QM-calculated value for the selected material property. Any suitable QM method can be used, such as those described above. After performing the QM calculation, method 200 comprises, at 232, outputting the QM-calculated value for the selected material property. As indicated by the arrow 228, the QM calculated value for the selected material property can be added to the materials information database. In this manner, the materials information database can be enhanced with QM calculated values for material properties. In some examples, the method comprises forming a material record comprising a QM-calculated value, and outputting the material record to a user account on of the materials information database.

Further, in some scenarios, a user may want more certain values than those predicted in a prior machine learning prediction for a generated material. Thus, the user may input a request to perform a QM calculation on the generated material. Upon performing the QM calculation, the calculated material property value(s) can be stored in an account of the user on the interactive material discovery platform. In this manner, a user of the materials information database can obtain QM-calculated values upon request. Alternatively or additionally, results of QM calculations requested by a user can be output to the materials information database.

In some examples, method 200 comprises, at 234, outputting the QM-calculated value for the material property to be used as training data for training a corresponding machine learning model. For example, a QM-calculated value of a bandgap can be used to further train a machine learning model configured for predicting a bandgap of a material. In this manner, the machine learning models can be improved in response to a user query.

Figure 5A:
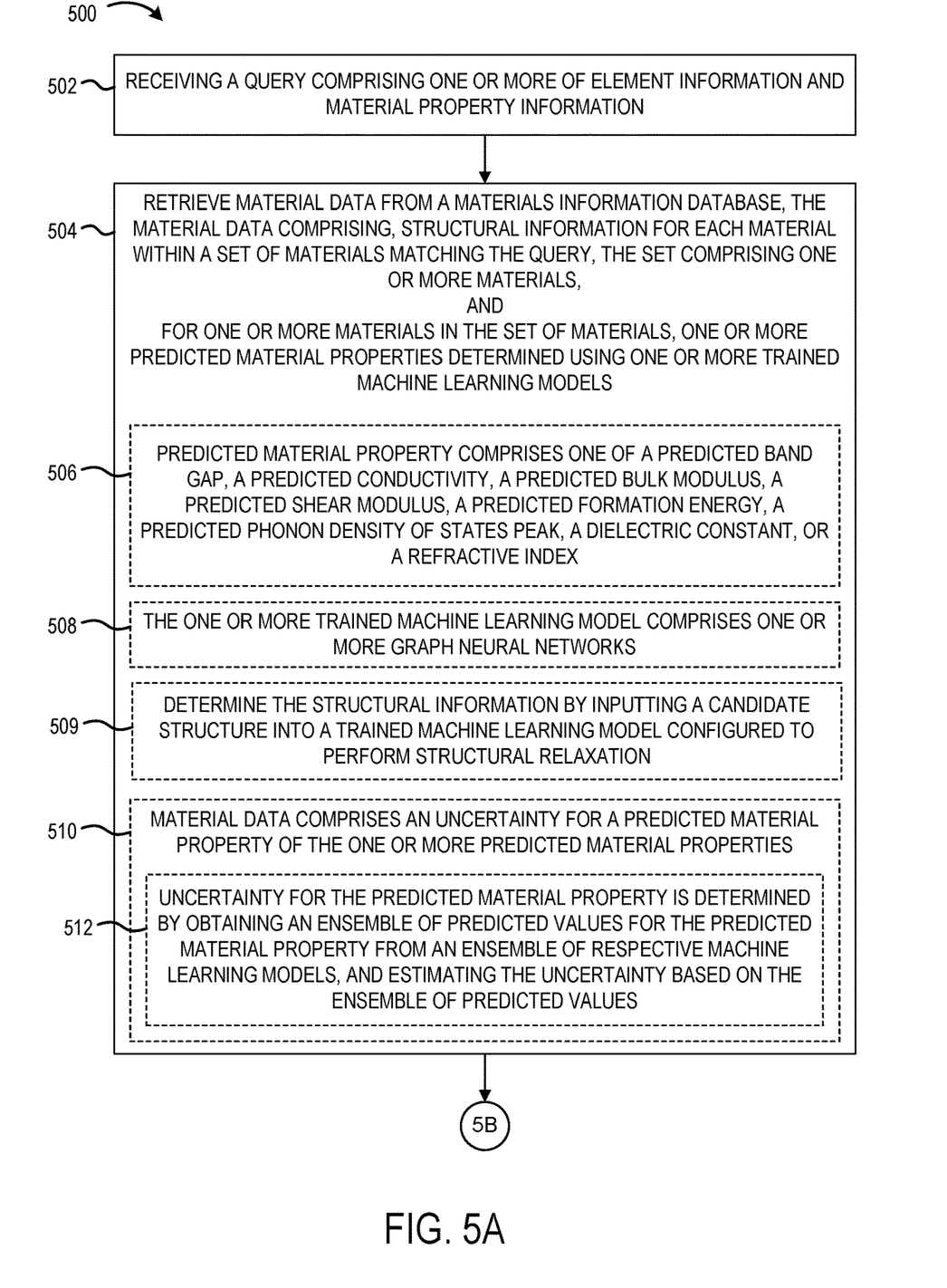
FIGS. 5A-5B show a flow diagram for an example method of processing a materials information database query.
Figure 5B:
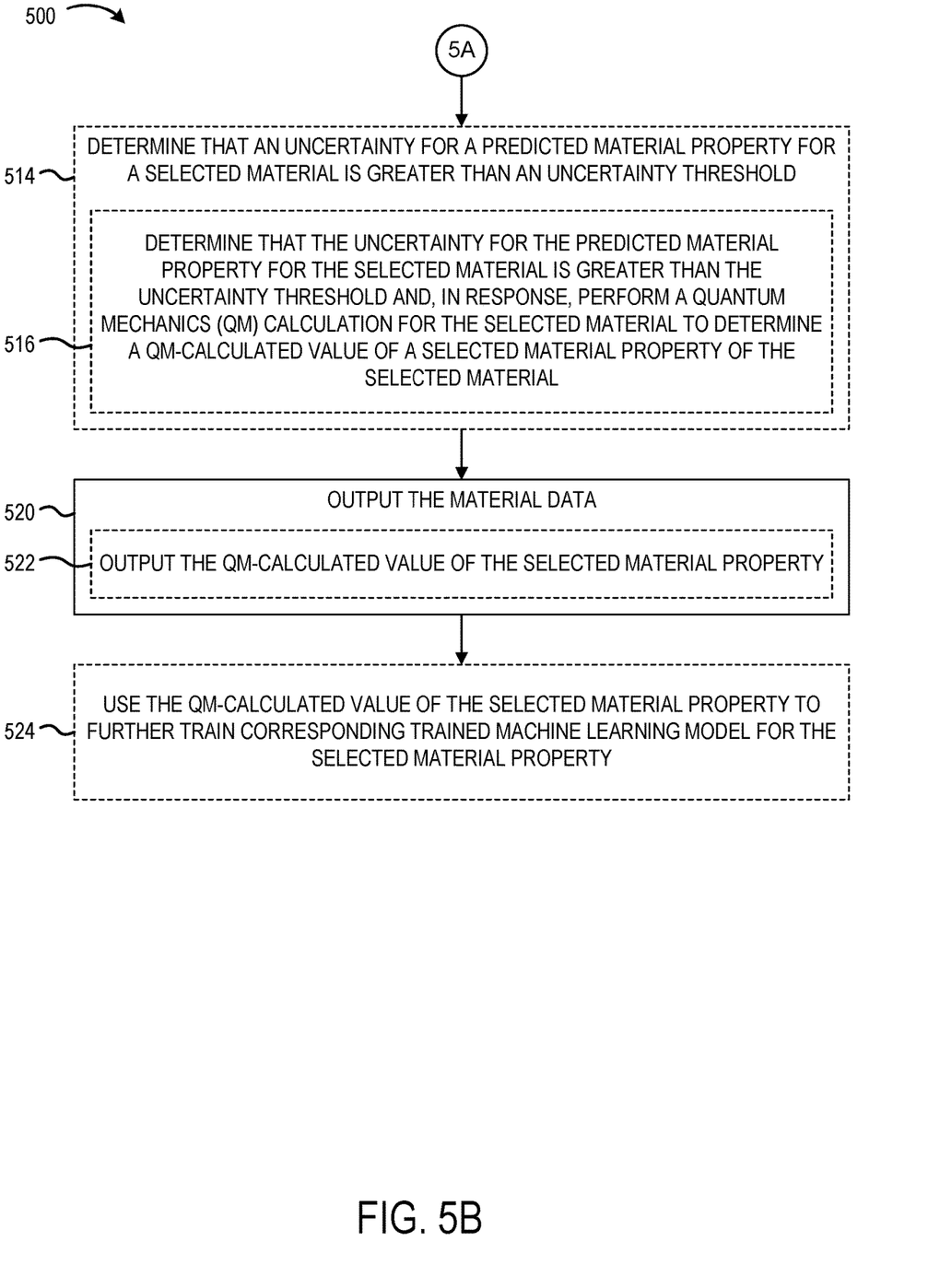

FIGS. 5A-5B show a flow diagram for an example method 500 of processing a query that includes retrieving material data from a materials information database comprising predicted material properties. Method 500 can be enacted on a computing system, such as remote computing system 104, configured to process user queries from client computers.

Referring to FIG. 5A, method 500 comprises, at 502, receiving a query comprising one or more of element information and material property information. In some examples, method 500 comprises processing the query using a large language model. For example, the query can be input into a large language model to extract element information and/or material property information. At 504, method 500 comprises, based on the query, retrieving material data from a materials information database. The material data comprises structural information for each material within a set of materials matching the query, the set comprising one or more materials. The material data further comprises, for one or more materials in the set of materials, one or more predicted material properties determined using one or more trained machine learning models. Each machine learning model can be configured to determine a predicted value for a corresponding material property. In some examples, two or more machine learning models, or an ensemble of machine learning models, can be used to determine predicted values for a corresponding material property. In some examples, at 506, the predicted material property comprises one of predicted band gap, a predicted conductivity, a predicted bulk modulus, a predicted shear modulus, a predicted formation energy, a predicted phonon density of states peak, a predicted dielectric constant, or a predicted refractive index. In some examples, at 508, the one or more trained machine learning models comprises one or more graph neural networks.

In some examples, at 509, method 500 comprises, for a material matching the query, determining the structural information by inputting a candidate structure into a trained machine learning model configured to perform structural relaxation and output a relaxed candidate structure. As discussed above, candidate structures can be generated using a trained generative machine learning model.

In some examples, at 510, the material data comprises an uncertainty for a predicted material property. In some such examples, at 512, the uncertainty for the predicted material property is determined by obtaining an ensemble of predicted values for the predicted material property from an ensemble of respective machine learning models, and estimating the uncertainty based on the ensemble of predicted values. In other examples, the uncertainty can be computed using any other suitable method.

Continuing to FIG. 5B, method 500 optionally comprises, at 514, comparing an uncertainty for a predicted material property for a selected material to an uncertainty threshold. In some examples, at 516, method 500 comprises determining that the uncertainty for the predicted material property is greater than the uncertainty threshold. In response, method 500 comprises performing a QM calculation for the selected material to determine a QM-calculated value of a selected material property of the selected material.

Continuing, at 520, method 500 further comprises outputting the material data. In some examples, when a QM calculation is performed at 516, method 500 comprises, at 522, outputting the QM calculated value of the selected material property.

As mentioned above, in some examples, each predicted material property is predicted using a corresponding trained machine learning model. In some such examples, method 500 further comprises, at 524, using the QM-calculated value of a selected material property to further train the corresponding trained machine learning model for the selected material property.

Figure 6:
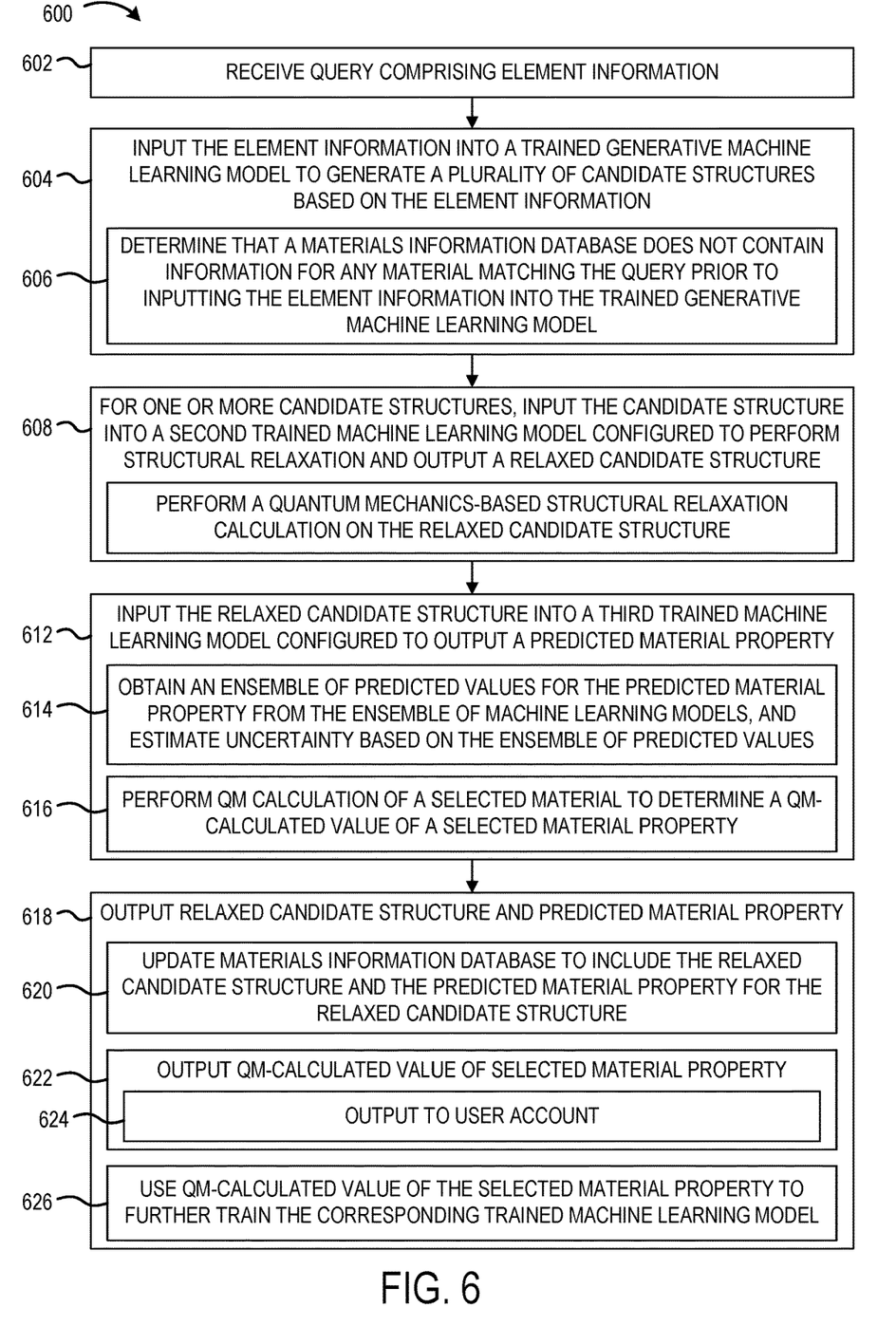
FIG. 6 shows a flow diagram for another example method of processing a materials information database query by using a machine learning model to generate a candidate structure of a material and predicting a material property for the candidate structure.

FIG. 6 shows a flow diagram for another example method 600 of processing a query that includes using a machine learning model to generate a candidate structure of a material and predicting a material property for a candidate structure. Method 600 can be enacted on any suitable computing system, such as remote computing system 104, configured to process user queries from client computers.

At 602, method 600 comprises receiving a query comprising element information. In some examples, method 600 comprises processing the query using a large language model. At 604, method 600 further comprises inputting the element information into a trained generative machine learning model to generate a plurality of candidate structures based on the element information. In some examples, at 606, method 600 comprises determining that a materials information database does not contain information for any material matching the query prior to inputting the element information into the trained generative machine learning model.

Method 600 further comprises, at 608, for one or more candidate structures generated at 604, inputting the candidate structure into a second trained machine learning model configured to perform structural relaxation and output a relaxed candidate structure. In some examples, at 610, method 600 comprises performing a QM-based structural relaxation calculation on the relaxed candidate structure. Any suitable QM method can be used, such as those listed above.

Continuing, method 600 further comprises, at 612, inputting the relaxed candidate structure into a third trained machine learning model configured to output a predicted material property. In some examples, at 614, the third trained machine learning model comprises an ensemble of trained machine learning models, and the method comprises obtaining an ensemble of predicted values for the predicted material property from the ensemble of machine learning models and estimating the uncertainty based on the ensemble of predicted values. In some examples, at 616, method 600 comprises performing a QM calculation of a selected material to determine a QM-calculated value of a selected material property.

Method 600 further comprises, at 618, outputting the relaxed candidate structure and the predicted material property. In some examples, at 620, method 600 comprises updating the materials information database to include the relaxed candidate structure and the predicted material property for the relaxed candidate structure. In examples where a QM calculation is performed at 616, method 600 comprises, at 622, outputting the QM-calculated value of the selected material property. In some such examples, at 624, method 600 comprises outputting the QM-calculated value to a user account of the interactive materials discovery platforms. In some examples, each predicted material property is predicted using a corresponding trained machine learning model. In some such examples, method 600 comprises, at 626, using the QM-calculated value of the selected material property to further train the corresponding trained machine learning model for the selected predicted material property.

In some embodiments, the methods and processes described herein may be tied to a computing system of one or more computing devices. In particular, such methods and processes may be implemented as a computer-application program or service, an application-programming interface (API), a library, and/or other computer-program product.

Figure 7:
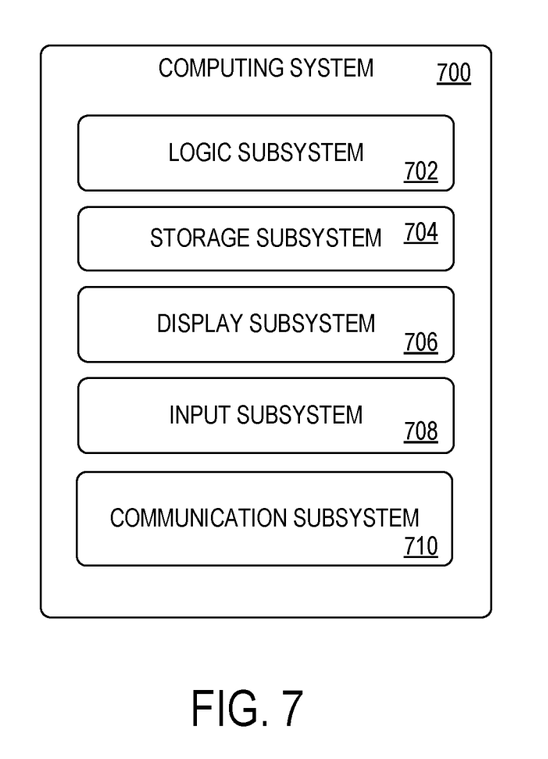
FIG. 7 shows a block diagram of an example computing system.

FIG. 7 schematically shows a simplified representation of a computing system 700 configured to provide any to all of the compute functionality described herein. Computing system 700 may take the form of one or more personal computers, server computers, and data centers, as examples. Remote computing system 104 is an example of computing system 700.

Computing system 700 includes a logic subsystem 702 and a storage subsystem 704. Computing system 700 may optionally include a display subsystem 706, input subsystem 708, communication subsystem 710, and/or other subsystems not shown in FIG. 7.

Logic subsystem 702 includes one or more physical devices configured to execute instructions. For example, the logic subsystem 702 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic subsystem 702 may include one or more hardware processors configured to execute software instructions. Additionally, or alternatively, the logic subsystem 702 may include one or more hardware or firmware devices configured to execute hardware or firmware instructions. Processors of the logic subsystem 702 may be single-core or multi-core, and the instructions executed thereon may be configured for sequential, parallel, and/or distributed processing. Individual components of the logic subsystem 702 optionally may be distributed among two or more separate devices, which may be remotely located and/or configured for coordinated processing. Aspects of the logic subsystem 702 may be virtualized and executed by remotely accessible, networked computing devices configured in a cloud-computing configuration.

Storage subsystem 704 includes one or more physical devices configured to temporarily and/or permanently hold computer information such as data and instructions executable by the logic subsystem 702. When the storage subsystem 704 includes two or more devices, the devices may be collocated and/or remotely located. Storage subsystem 704 may include volatile, nonvolatile, dynamic, static, read/write, read-only, random-access, sequential-access, location-addressable, file-addressable, and/or content-addressable devices. Storage subsystem 704 may include removable and/or built-in devices. When the logic subsystem 702 executes instructions, the state of storage subsystem 704 may be transformed—e.g., to hold different data.

Storage subsystem 704 may include removable and/or built-in devices. Storage subsystem 704 may include optical memory (e.g., CD, DVD, HD-DVD, Blu-Ray Disc, etc.), semiconductor memory (e.g., RAM, EPROM, EEPROM, etc.), and/or magnetic memory, among others. Storage subsystem 704 may include volatile, nonvolatile, dynamic, static, read/write, read-only, random-access, sequential-access, location-addressable, file-addressable, and/or content-addressable devices.

Aspects of logic subsystem 702 and storage subsystem 704 may be integrated together into one or more hardware-logic components. Such hardware-logic components may include program- and application-specific integrated circuits (PASIC/ASICs), program- and application-specific standard products (PSSP/ASSPs), system-on-a-chip (SOC), and complex programmable logic devices (CPLDs), for example.

It will be appreciated that the storage subsystem 704 includes one or more physical devices. However, aspects of the instructions described herein alternatively may be propagated by a communication medium (e.g., an electromagnetic signal, an optical signal, etc.) that is not held by a physical device for a finite duration.

The logic subsystem 702 and the storage subsystem 704 may cooperate to instantiate one or more logic machines. As used herein, the term "machine" is used to collectively refer to the combination of hardware, firmware, software, instructions, and/or any other components cooperating to provide computer functionality. A machine may be instantiated by a single computing device, or a machine may include two or more sub-components instantiated by two or more different computing devices. In some implementations a machine includes a local component (e.g., software application executed by a computer processor) cooperating with a remote component (e.g., cloud computing service provided by a network of server computers). The software and/or other instructions that give a particular machine its functionality may optionally be saved as one or more unexecuted modules on one or more suitable storage devices.

The terms "module" and "program" may be used to describe an aspect of computing system 700 implemented to perform a particular function. In some cases, a module, program, or engine may be instantiated via logic subsystem 702 executing instructions held by storage subsystem 704. It will be understood that different modules and/or programs may be instantiated from the same application, service, code block, object, library, routine, API, function, etc. Likewise, the same module and/or program may be instantiated by different applications, services, code blocks, objects, routines, APIs, functions, etc. The terms "module" and "program" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 706 may be used to present a visual representation of data held by storage subsystem 704. This visual representation may take the form of a graphical user interface (GUI). As the herein described methods and processes change the data held by the storage subsystem 704, and thus transform the state of the storage subsystem 704, the state of display subsystem 706 may likewise be transformed to visually represent changes in the underlying data. Display subsystem 706 may include one or more display devices utilizing virtually any type of technology. Such display devices may be combined with the logic subsystem 702 and the storage subsystem 704 in a shared enclosure, or such display devices may be peripheral display devices.

When included, input subsystem 708 may comprise or interface with one or more input devices such as a keyboard, mouse, touch screen. In some examples, the input subsystem 708 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; and an infrared, color, stereoscopic, and/or depth camera for machine vision and/or gesture recognition. In some examples, an interface comprises a large language model, which can be used in processing user queries, for example.

When included, communication subsystem 710 may be configured to communicatively couple computing system 700 with one or more other computing devices. Communication subsystem 710 may include wired and/or wireless communication devices compatible with one or more different communication protocols. As non-limiting examples, the communication subsystem 710 may be configured for communication via a wireless telephone network, or a wired or wireless local- or wide-area network. In some examples, the communication subsystem 710 may allow computing system 700 to send and/or receive messages to and/or from other devices via a network such as the Internet.

Another example provides a method enacted on a computing system. The method comprises receiving a query comprising one or more of element information and material property information. The method further comprises, based on the query, retrieving material data from a materials information database, the material data comprising, structural information for each material within a set of materials matching the query, the set comprising one or more materials, and, for one or more materials in the set of materials, one or more predicted material properties determined using one or more trained machine learning models. The method further comprises outputting the material data. In some such examples, the method further comprises determining that an uncertainty for a predicted material property for a selected material is greater than an uncertainty threshold, in response, performing a quantum mechanics (QM) calculation for the selected material to determine a QM-calculated value of a selected material property of the selected material, and outputting the QM-calculated value of the selected material property. In some such examples, each predicted material property alternatively or additionally is predicted using a corresponding trained machine learning model, and further comprising using the QM-calculated value of the selected material property to further train the corresponding trained machine learning model for the selected predicted material property. In some such examples, the method alternatively or additionally comprises, for a material matching the query, determining the structural information by inputting a candidate structure into a trained machine learning model configured to perform structural relaxation and output a relaxed candidate structure. In some such examples, the predicted material property alternatively or additionally comprises one of a predicted band gap, a predicted conductivity, a predicted bulk modulus, a predicted shear modulus, a predicted formation energy, a predicted phonon density of states peak, a dielectric constant, or a refractive index. In some such examples, the one or more trained machine learning model alternatively or additionally comprises one or more graph neural networks. In some such examples, the material data alternatively or additionally comprises an uncertainty for a predicted material property of the one or more predicted material properties. In some such examples, the uncertainty for the predicted material property alternatively or additionally is determined by obtaining an ensemble of predicted values for the predicted material property from an ensemble of respective machine learning models, and estimating the uncertainty based on the ensemble of predicted values. In some such examples, receiving the query alternatively or additionally comprises inputting the query into a large language model configured to extract the one or more of element information or material property information.

Another example provides a method enacted on a computing system, the method comprising receiving a query comprising element information and inputting the element information into a trained generative machine learning model to generate a plurality of candidate structures based on the element information. The method further comprises, for one or more candidate structures of the plurality of candidate structures, inputting the candidate structure into a second trained machine learning model configured to perform structural relaxation and output a relaxed candidate structure, inputting the relaxed candidate structure into a third trained machine learning model configured to output a predicted material property, and outputting the relaxed candidate structure and the predicted material property. In some such examples, the method further comprises determining that a materials information database does not contain information for any material matching the query prior to inputting the element information into the trained generative machine learning model. In some such examples, the method alternatively or additionally comprises updating the materials information database to include the relaxed candidate structure and the predicted material property for the relaxed candidate structure. In some such examples, the third trained machine learning model alternatively or additionally comprises an ensemble of trained machine learning models, and the method comprises obtaining an ensemble of predicted values for the predicted material property from the ensemble of machine learning models, and estimating the uncertainty based on the ensemble of predicted values. In some such examples, the method alternatively or additionally comprises performing a quantum mechanics (QM) calculation of a selected material to determine a QM-calculated value of a selected material property, and outputting the QM-calculated value of the selected material property. In some such examples, each predicted material property alternatively or additionally is predicted using a corresponding trained machine learning model, and further comprising using the QM-calculated value of the selected material property to further train the corresponding trained machine learning model for the selected predicted material property.

Another example provides a computing system, comprising a logic subsystem and a storage subsystem holding instructions executable by the logic subsystem to receive a query comprising element information, and input the element information into a trained generative machine learning model to generate a plurality of candidate structures based on the element information. The instructions are further executable to, for one or more candidate structures of the plurality of candidate structures, input the candidate structure into a second trained machine learning model configured to perform structural relaxation and output a relaxed candidate structure, input the relaxed candidate structure into a third trained machine learning model configured to output a predicted material property, and output the relaxed candidate structure and the predicted material property. In some such examples, the instructions are further executable to determine that a materials information database does not contain information for any material matching the query prior to inputting the element information into the trained generative machine learning model. In some such examples, the instructions alternatively or additionally are further executable to update the materials information database to include the relaxed candidate structure and the predicted material property for the candidate structure. In some such examples, the instructions alternatively or additionally are further executable to input the query into a large language model configured to extract the element information. In some such examples, the instructions alternatively or additionally are further executable to receive a user input requesting to perform a QM calculation for the relaxed candidate structure to determine a QM-calculated value of a selected material property, form a material record comprising structural information based on the relaxed candidate structure and the QM-calculated value of the selected material property, and output the material record for storage in an account of the user.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method enacted on a computing system, the method comprising:
   receiving a query comprising one or more of element information and material property information;
   based on the query, retrieving material data from a materials information database, the material data comprising,
      structural information for each material within a set of materials matching the query, the set comprising one or more materials, and
      for one or more materials in the set of materials, one or more predicted material properties determined using one or more trained machine learning models; and
   outputting the material data.

2. The method of claim 1, further comprising
   determining that an uncertainty for a predicted material property for a selected material is greater than an uncertainty threshold;
   in response, performing a quantum mechanics (QM) calculation for the selected material to determine a QM-calculated value of a selected material property of the selected material; and
   outputting the QM-calculated value of the selected material property.

3. The method of claim 2, wherein each predicted material property is predicted using a corresponding trained machine learning model, and further comprising using the QM-calculated value of the selected material property to further train the corresponding trained machine learning model for the selected predicted material property.

4. The method of claim 1, further comprising, for a material matching the query, determining the structural information by inputting a candidate structure into a trained machine learning model configured to perform structural relaxation and output a relaxed candidate structure.

5. The method of claim 1, wherein the predicted material property comprises one of a predicted band gap, a predicted conductivity, a predicted bulk modulus, a predicted shear modulus, a predicted formation energy, a predicted phonon density of states peak, a dielectric constant, or a refractive index.

6. The method of claim 1, wherein the one or more trained machine learning model comprises one or more graph neural networks.

7. The method of claim 1, wherein the material data comprises an uncertainty for a predicted material property of the one or more predicted material properties.

8. The method of claim 7, wherein the uncertainty for the predicted material property is determined by obtaining an ensemble of predicted values for the predicted material property from an ensemble of respective machine learning models, and estimating the uncertainty based on the ensemble of predicted values.

9. The method of claim 1, wherein receiving the query comprises inputting the query into a large language model configured to extract the one or more of element information or material property information.

10. A method enacted on a computing system, the method comprising:
    receiving a query comprising element information;
    inputting the element information into a trained generative machine learning model to generate a plurality of candidate structures based on the element information; and
    for one or more candidate structures of the plurality of candidate structures
        inputting the candidate structure into a second trained machine learning model configured to perform structural relaxation and output a relaxed candidate structure,
        inputting the relaxed candidate structure into a third trained machine learning model configured to output a predicted material property, and
        outputting the relaxed candidate structure and the predicted material property.

11. The method of claim 10, further comprising determining that a materials information database does not contain information for any material matching the query prior to inputting the element information into the trained generative machine learning model.

12. The method of claim 11, further comprising updating the materials information database to include the relaxed candidate structure and the predicted material property for the relaxed candidate structure.

13. The method of claim 10, wherein the third trained machine learning model comprises an ensemble of trained machine learning models, and the method comprise
    obtaining an ensemble of predicted values for the predicted material property from the ensemble of machine learning models, and
    estimating the uncertainty based on the ensemble of predicted values.

14. The method of claim 10, further comprising
    performing a quantum mechanics (QM) calculation of a selected material to determine a QM-calculated value of a selected material property, and
    outputting the QM-calculated value of the selected material property.

15. The method of claim 14, wherein each predicted material property is predicted using a corresponding trained machine learning model, and further comprising using the QM-calculated value of the selected material property to further train the corresponding trained machine learning model for the selected predicted material property.

16. A computing system, comprising:
    a logic subsystem; and
    a storage subsystem holding instructions executable by the logic subsystem to:
        receive a query comprising element information,
        input the element information into a trained generative machine learning model to generate a plurality of candidate structures based on the element information; and
        for one or more candidate structures of the plurality of candidate structures
            input the candidate structure into a second trained machine learning model configured to perform structural relaxation and output a relaxed candidate structure,
            input the relaxed candidate structure into a third trained machine learning model configured to output a predicted material property, and
            output the relaxed candidate structure and the predicted material property.

17. The computing system of claim 16, wherein the instructions are further executable to determine that a materials information database does not contain information for any material matching the query prior to inputting the element information into the trained generative machine learning model.

18. The computing system of claim 17, wherein the instructions are further executable to update the materials information database to include the relaxed candidate structure and the predicted material property for the candidate structure.

19. The computing system of claim 16, wherein the instructions are further executable to input the query into a large language model configured to extract the element information.

20. The computing system of claim 16, wherein the instructions are further executable to
    receive a user input requesting to perform a QM calculation for the relaxed candidate structure to determine a QM-calculated value of a selected material property,
    form a material record comprising structural information based on the relaxed candidate structure and the QM-calculated value of the selected material property, and
    output the material record for storage in an account of the user.

* * * * *